United States Patent
Khanafer et al.

(10) Patent No.: US 8,930,086 B2
(45) Date of Patent: Jan. 6, 2015

(54) DRIVER ASSISTANCE SYSTEM FOR A MOTOR VEHICLE, MOTOR VEHICLE, AND METHOD FOR OPERATING A DRIVER ASSISTANCE SYSTEM

(75) Inventors: Ali Khanafer, Mainz (DE); Oliver Schepp, Idstein (DE); Markus Friesen, Gross-Gerau (DE); Oliver Roettel, Buettelborn (DE)

(73) Assignee: GM Global Technology Operations LLC, Detroit, MI (US)

( * ) Notice: Subject to any disclaimer, the term of this patent is extended or adjusted under 35 U.S.C. 154(b) by 127 days.

(21) Appl. No.: 13/338,295

(22) Filed: Dec. 28, 2011

(65) Prior Publication Data

US 2012/0166047 A1 Jun. 28, 2012

(30) Foreign Application Priority Data

Dec. 28, 2010 (DE) .......................... 10 2010 056 397

(51) Int. Cl.
- *B60R 22/00* (2006.01)
- *E05F 15/20* (2006.01)
- *B60H 1/00* (2006.01)
- *A61B 5/18* (2006.01)

(52) U.S. Cl.
CPC ....... *E05F 15/2015* (2013.01); *E05Y 2400/358* (2013.01); *A61B 5/18* (2013.01); *E05Y 2201/422* (2013.01); *E05Y 2900/55* (2013.01); *B60H 1/00735* (2013.01)
USPC .......................................... 701/48; 180/333

(58) Field of Classification Search
USPC ........ 701/48, 70; 340/575, 576; 180/179, 333
See application file for complete search history.

(56) References Cited

U.S. PATENT DOCUMENTS

| 7,202,792 B2 * | 4/2007 | Zhang et al. .................. 340/575 |
| 8,301,108 B2 * | 10/2012 | Naboulsi ...................... 455/345 |
| 2002/0101354 A1 * | 8/2002 | Banas ........................... 340/576 |
| 2004/0201481 A1 | 10/2004 | Yoshinori et al. |
| 2009/0255645 A1 | 10/2009 | Ladstaetter |
| 2010/0312446 A1 * | 12/2010 | Schofield et al. .............. 701/70 |

FOREIGN PATENT DOCUMENTS

| DE | 19822676 A1 | 12/1999 |
| DE | 10233727 C1 | 12/2003 |
| DE | 10233726 A1 | 2/2004 |
| DE | 102004022581 A1 | 4/2005 |
| DE | 102006006436 A1 | 8/2007 |

(Continued)

OTHER PUBLICATIONS

UK IPO, British Search Report for Application No. 1121134.9, dated Apr. 23, 2012.

*Primary Examiner* — Thomas G Black
*Assistant Examiner* — Luke Huynh
(74) *Attorney, Agent, or Firm* — Ingrassia Fisher & Lorenz, P.C.

(57) ABSTRACT

A driver assistance system is provided for a motor vehicle, which has a first ascertainment device, the first ascertainment device implemented to ascertain at least one parameter that characterizes a possible fatigue of a current driver of the motor vehicle. In addition, the driver assistance system has a second ascertainment device, which is implemented to ascertain a degree of fatigue of the driver based on the at least one ascertained parameter. In addition, the driver assistance system has an opening device, which is implemented to at least partially open at least one window of the motor vehicle if the ascertained degree of fatigue of the driver exceeds a first predetermined threshold value.

13 Claims, 5 Drawing Sheets

(56) References Cited

FOREIGN PATENT DOCUMENTS

| DE | 102008007149 A1 | 10/2008 |
| DE | 102007046037 B3 | 4/2009 |
| DE | 102009016936 A1 | 11/2009 |
| DE | 102010004089 A1 | 9/2010 |
| EP | 1418082 A1 | 5/2004 |
| GB | 1495065 A | 12/1977 |
| GB | 2324864 A | 11/1998 |
| KR | 20020014445 A | 2/2002 |

* cited by examiner

DRIVER ASSISTANCE SYSTEM FOR A MOTOR VEHICLE, MOTOR VEHICLE, AND METHOD FOR OPERATING A DRIVER ASSISTANCE SYSTEM

CROSS-REFERENCE TO RELATED APPLICATION

This application claims priority to German Patent Application No. 102010056397.8, filed Dec. 28, 2010, which is incorporated herein by reference in its entirety.

TECHNICAL FIELD

The technical field relates to a driver assistance system for a motor vehicle, a motor vehicle having a driver assistance system, a method for operating a driver assistance system of a motor vehicle, a computer program product, and a computer-readable medium.

BACKGROUND

A device for climate control is known from DE 10 2006 006 436 A1. The device for climate control has at least one data interface for outputting first control data for a positioning unit of an air supply into a foot well of the driver such that the foot well is cooled in relation to the remaining surroundings of the driver. In addition, the data interface serves to output second control data to a means for heating the remaining surroundings of the driver such that the remaining surroundings of the driver are at least partially heated and therefore the physiological chain of action that begins in the event of fatigue of the driver is interrupted.

At least one object is to specify a driver assistance system for a motor vehicle, a motor vehicle, a method for operating a driver assistance system of a motor vehicle, a computer program product, and a computer-readable medium, which allow an increase of the driving safety. In addition, other objects, desirable features, and characteristics will become apparent from the subsequent summary and detailed description, and the appended claims, taken in conjunction with the accompanying drawings and this background.

SUMMARY

According to an embodiment, a driver assistance system is provided for a motor vehicle has a first ascertainment device, which is implemented to ascertain at least one parameter that characterizes a possible fatigue of a current driver of the motor vehicle. In addition, the driver assistance system has a second ascertainment device, which is implemented to ascertain a degree of fatigue of the driver based on the at least one ascertained parameter. In addition, the driver assistance system has an opening device, which is implemented to at least partially open at least one window of the motor vehicle, if the ascertained degree of fatigue of the driver exceeds a first predetermined threshold value.

The driver assistance system according to the embodiment allows an increase of the driving safety in that the opening device is implemented to at least partially open at least one window of the motor vehicle, if the ascertained degree of fatigue of the driver exceeds a first predetermined threshold value. Consideration is given to the air quality in the interior of the motor vehicle can be improved by the at least partial opening of the at least one window, in particular in that the supplied outside air typically has a higher oxygen content than the air already present in the interior of the motor vehicle. This allows a recovery of driver attentiveness or a prevention of driver fatigue. The safety of the driver can thus be increased.

The at least one window is preferably a side window arranged on the driver's side in a front area of the motor vehicle. The supplied outside air can thus advantageously flow as directly as possible against the driver of the motor vehicle.

In a further embodiment, the driver assistance system is implemented to reduce a temperature, which is set by means of an air conditioner of the motor vehicle, of at least one subarea of the interior of the motor vehicle, if the ascertained degree of fatigue of the driver exceeds the first predetermined threshold value. Additionally or alternatively, the driver assistance system can be implemented to increase a fresh air component, which is set by means of the air conditioner of the motor vehicle, of at least one subarea of the interior of the motor vehicle, if the ascertained degree of fatigue of the driver exceeds the first predetermined threshold value. Fresh air is to be understood here and hereafter as filtered and optionally dehumidified and/or cooled outside air. The mentioned embodiments allow the recovery of the driver attentiveness or the reduction of the driver fatigue to be supported further by the control or regulation of the temperature and/or the air quality inside the motor vehicle by means of the air conditioner.

In the mentioned embodiments, the subarea of the interior of the motor vehicle preferably at least partially contains an area of surroundings of the driver. The driver can thus be supported to a large extent in the recovery of his attentiveness by the temperature reduction or the improvement of the air quality.

In a further embodiment, the driver assistance system is additionally implemented to increase a direct flow against the driver using fresh air provided by means of the air conditioner of the motor vehicle, if the ascertained degree of fatigue of the driver exceeds the first predetermined threshold value. This advantageously in turn results in a provision of the fresh air directly to the driver. The driver assistance system is additionally preferably implemented to ascertain a current weather situation in the surroundings of the motor vehicle by means of data of at least one sensor. The opening device is implemented in this embodiment to at least partially open the at least one window of the motor vehicle, if the ascertained degree of fatigue of the driver exceeds the first predetermined threshold value and if it is ascertained that the current weather situation in the surroundings of the motor vehicle is free of precipitation. Penetration of moisture into the vehicle interior in the event of bad weather conditions, for example, in the event of rain, snow, hail, sleet, or fog, and misting of the inside of the windows possibly connected to the penetration can be prevented.

The at least one sensor is preferably implemented as an optoelectronic and/or capacitive rain sensor. Such rain sensors are provided to an increased extent in motor vehicles, whereby the number of additionally required components of the driver assistance system can advantageously be reduced.

Additionally or alternatively, the driver assistance system can be implemented to ascertain a current weather situation in the surroundings of the motor vehicle by means of data received by a vehicle-to-vehicle and/or vehicle-to-infrastructure communication device. The opening device is in turn implemented to at least partially open the at least one window of the motor vehicle if the ascertained degree of fatigue of the driver exceeds the first predetermined threshold value and if it is ascertained that the current weather situation in the surroundings of the motor vehicle is free of precipitation. Furthermore, the mentioned data can be fused and checked for plausibility.

The at least one parameter which characterizes a possible fatigue of the current driver of the motor vehicle is preferably selected from the group consisting of a closing frequency of at least one eyelid of the driver, a closing speed of the at least one eyelid of the driver, a body temperature of the driver, a pulse rate of the driver, a frequency of steering movements performed by the driver, and a time curve of steering movements performed by the driver. For this purpose, the driver assistance system has one or more sensors implemented in such a manner, for example, an optical camera, and/or a steering angle sensor. The mentioned parameters allow the degree of fatigue of the driver to be ascertained to the most precise possible extent.

Furthermore, the second ascertainment device can be implemented to ascertain a degree of fatigue of the driver based on at least one ascertained parameter and based on a current time of day. This proceeds from the consideration that the fatigue of the driver can differ at different times of day. For example, the fatigue is higher in the evening or at night than during the day.

The application additionally relates to a motor vehicle having a driver assistance system according to one of the mentioned embodiments. The motor vehicle is preferably a passenger automobile or a truck. In addition, the application relates to a method for operating a driver assistance system of a motor vehicle, the method having the following steps. An ascertainment of at least one parameter, which characterizes a possible fatigue of a current driver of the motor vehicle, is performed. In addition, an ascertainment of a degree of fatigue of the driver is performed based on the at least one ascertained parameter. If the ascertained degree of fatigue of the driver exceeds a first predetermined threshold value, at least partial opening of at least one window of the vehicle is performed by means of at least one opening device. The motor vehicle and the method according to the application have the advantages already mentioned in connection with the driver assistance system according to the application, which will not be listed again at this point to avoid repetitions.

In a preferred embodiment of the method, in addition, a temperature Texterior of the ambient air outside the motor vehicle and a temperature Tinterior of the interior of the motor vehicle are ascertained. The at least partial opening of the at least one window of the motor vehicle is performed in this embodiment if the ascertained degree of fatigue of the driver exceeds the first predetermined threshold value and if Tinterior>Texterior. The mentioned embodiment proceeds from the consideration that recovering the driver attentiveness, preventing, or reducing the driver fatigue can be made possible to a particularly high extent by supplying outside air, if the temperature of the ambient air outside the motor vehicle is lower than the temperature of the interior of the motor vehicle.

In a further embodiment of the method, a first warning message is also output if the ascertained degree of fatigue of the driver exceeds the first predetermined threshold value. The driver and/or further occupants of the motor vehicle can thus be notified of the possible fatigue of the driver. The first warning application is preferably output as an optical and/or acoustic and/or haptic warning message. For example, a display of warning signals can be performed in a display device of an information and entertainment system of the motor vehicle and/or in an instrument cluster of the motor vehicle. Additionally or alternatively, a playback of warning tones, in particular at different volumes and at different frequencies, can be performed. Furthermore, a haptic warning message can be performed, for example, by vibration of a steering wheel and/or a brake or accelerator pedal of the motor vehicle and/or of the driver's seat.

In a further embodiment, a second warning message is output if the ascertained degree of fatigue of the driver exceeds a second predetermined threshold value, the second predetermined threshold value being lower than the first predetermined threshold value. The second warning message can be output as an optical and/or acoustic and/or haptic warning message. The driver or further occupants of the motor vehicle can thus advantageously already be notified thereof in the event of slight appearances of fatigue of the driver.

One type of the output of the first warning message and/or the second warning message can additionally be selected as a function of the ascertained degree of fatigue. This allows a further differentiation of the output of the corresponding warning message based on the ascertained degree of fatigue Furthermore, the application relates to a computer program product, which, when it is executed on a computer unit of a motor vehicle, instructs the computer unit to execute the following steps. The computer unit is instructed to ascertain at least one parameter characterizing a possible fatigue of a current driver of the motor vehicle. In addition, the computer unit is instructed to ascertain a degree of fatigue of the driver based on the at least one ascertained parameter. If the ascertained degree of fatigue of the driver exceeds a first predetermined threshold value, the computer unit is instructed to at least partially open at least one window of the motor vehicle by means of at least one opening device. Furthermore, the application relates to a computer-readable medium, on which a computer program product according to the mentioned embodiment is stored. The computer program product and the computer-readable medium according to the application have the advantages already mentioned in connection with the driver assistance system, which will not be listed once again at this point to avoid repetitions.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit application and uses. Furthermore, there is no intention to be bound by any theory presented in the preceding background or summary or the following detailed description.

Figure 1:
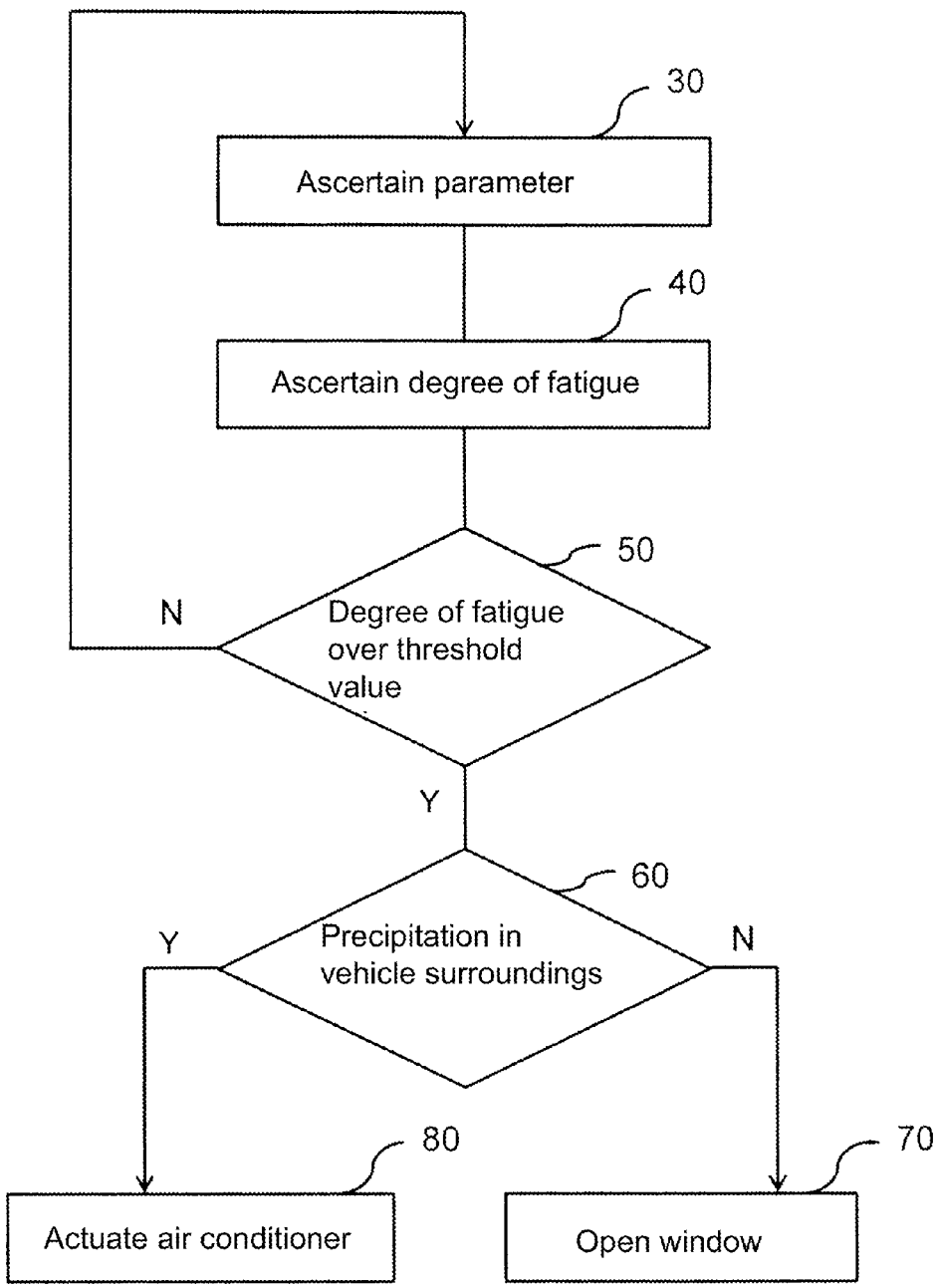
FIG. 1 shows a flowchart of a method for operating a driver assistance system of a motor vehicle according to a first embodiment.

FIG. 1 shows a flowchart of a method for operating a driver assistance system of a motor vehicle according to a first embodiment. The motor vehicle is a passenger automobile or a truck, for example. In a step 30, an ascertainment of at least one parameter, which characterizes a possible fatigue of a current driver of the motor vehicle, is performed. The at least one parameter which characterizes a possible fatigue of the current driver of the motor vehicle is preferably selected from the group consisting of a closing frequency of at least one eyelid of the driver, a closing speed of the at least one eyelid of the driver, a body temperature of the driver, a pulse rate of the driver, a frequency of steering movements performed by the driver, and a time curve of steering movements performed by the driver.

In a step 40, an ascertainment of a degree of fatigue of the driver is performed based on the at least one ascertained parameter. For example, a high degree of fatigue can be concluded from the time curve of the performed steering movements if the steering movements occur suddenly. In addition, an elevated degree of fatigue can exist if the pulse rate is below a predetermined threshold value for a predetermined duration, for example.

In a step 50, it is checked whether the ascertained degree of fatigue of the driver exceeds a first predetermined threshold value. If the ascertained degree of fatigue of the driver does not exceed the first predetermined threshold value, in the embodiment shown, the steps 30, 40, and 50 are executed repeatedly. In contrast, if the ascertained degree of fatigue of the driver exceeds the first predetermined threshold value, in a step 60, a current weather situation in the surroundings of the motor vehicle is ascertained and it is monitored whether the current weather situation in the surroundings of the motor vehicle is free of precipitation. This is preferably performed by means of data of an optoelectronic and/or capacitor rain sensor of the motor vehicle. The motor vehicle can additionally have further sensors, for example, light sensors, which are arranged in a common housing with the rain sensor, for example. Furthermore, the current weather situation in the surroundings of the motor vehicle can be ascertained by means of data received by a vehicle-to-vehicle and/or vehicle-to-infrastructure communication device.

If it is ascertained in step 60 that the current weather situation in the surroundings of the motor vehicle is free of precipitation, at least partial opening of at least one window of the motor vehicle is performed in a step 70 by means of at least one opening device, for example, by means of an electric motor. The at least one window is preferably a side window arranged in a front area of the motor vehicle on the driver's side. If the at least one window has already previously been at least partially opened, further opening of the at least one window and/or at least partial opening of at least one further window of the motor vehicle are performed in step 70. Furthermore, all windows of the motor vehicle can be at least partially opened in step 70.

In contrast, if it is ascertained in step 60 that the current weather situation in the surroundings of the motor vehicle is not free of precipitation, an actuation of an air conditioner of the motor vehicle is performed by means of the driver assistance system in a step 80 in such a manner that a reduction of a temperature, which is set by means of the air conditioner, of at least one subarea of the interior of the motor vehicle and/or an increase of a fresh air component, which is set by means of the air conditioner of the motor vehicle, of at least one subarea of the interior of the motor vehicle is performed. The subarea of the interior of the motor vehicle preferably at least partially includes an area of the immediate surroundings of the driver. In addition, a higher level of the ventilation and/or a direct flow of fresh air against the driver can be performed.

In addition, a warning message can additionally be output in steps 70 and 80, for example, an optical and/or acoustic and/or haptic warning message. The playback of warning tones can be performed at different volumes and at different frequencies. In addition, a haptic warning message can be performed, for example, by vibration of the steering wheel, by vibration of brake pedal and/or gas pedal, and/or by vibration of the driver seat.

Figure 2:
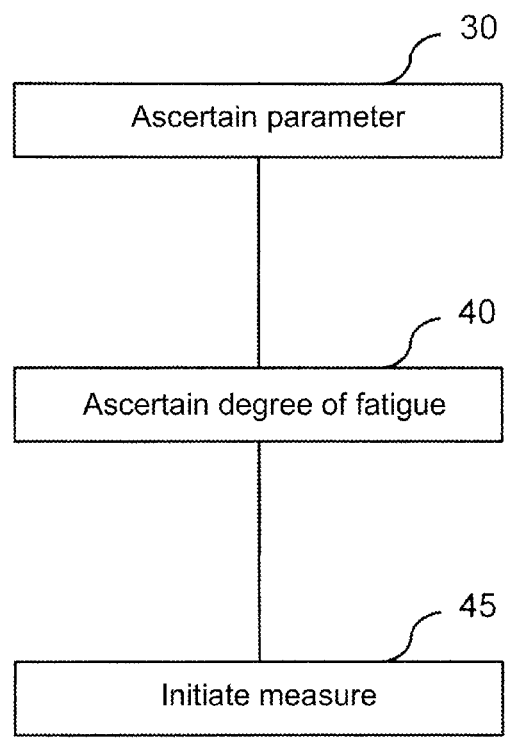
FIG. 2 shows a flowchart of a method for operating a driver assistance system of a motor vehicle according to a second embodiment.

2 shows a flowchart of a method for operating a driver assistance system of a motor vehicle according to a second embodiment. The motor vehicle is a passenger automobile or a truck, for example. In a step 30, an ascertainment of at least one parameter, which characterizes a possible fatigue of a current driver of the motor vehicle, is performed. Furthermore, in a step 40, an ascertainment of a degree of fatigue of the driver is performed based on the at least one ascertained parameter. Steps 30 and 40 of the second embodiment shown in FIG. 2 are performed corresponding to steps 30 and 40 of the first embodiment of the method shown in FIG. 1.

If fatigue of the driver is recognized during the travel, the driver is notified of the degree of fatigue in the embodiment shown by means of graduated warning messages. For this purpose, in a step 45, a determination and initiation of a measure to be carried out is performed. The driver assistance system follows a graduation from level 1 to level 4, which is explained hereafter, in the embodiment shown, level 1 denoting slight fatigue and level 4 denoting strong fatigue.

If the ascertained degree of fatigue of the driver corresponds to level 1, an optical warning message is output. In the embodiment shown, this is performed in the form of a display of a coffee cup symbol in an instrument cluster (IPC) of the motor vehicle. If the ascertained degree of fatigue of the driver corresponds to level 2, an acoustic warning message is performed, for example, a gong, in connection with a display in the instrument cluster (IPC). If the ascertained degree of fatigue of the driver corresponds to level 3, an optical warning message is performed in a display device of an information and entertainment system of the motor vehicle, for example, in an infotainment display, in connection with an acoustic warning message.

If the ascertained degree of fatigue of the driver corresponds to level 4, a temperature regulation is performed in the vehicle interior by activating the air conditioner and the ventilation flaps and by opening the window, corresponding to steps 70 and 80 of the first embodiment of the method shown in FIG. 1. Therefore, the temperature and air quality in the motor vehicle can be regulated in such a manner that fatigue of the driver can be temporarily prevented or reduced. On the one hand, this is performed by reducing the interior temperature by means of the air conditioner in connection with a higher level of the ventilation and a direct flow against the driver, on the other hand, this is performed by at least partially opening the window. Before opening of the window is performed in level 4, the weather conditions are checked by means of a rain/light sensor. For example, if rain or snow and therefore poor weather conditions are recognized, automatic opening of the window is prevented, to avoid the penetration of moisture into the vehicle interior, i.e., opening is only performed in dry weather.

Figure 3A:
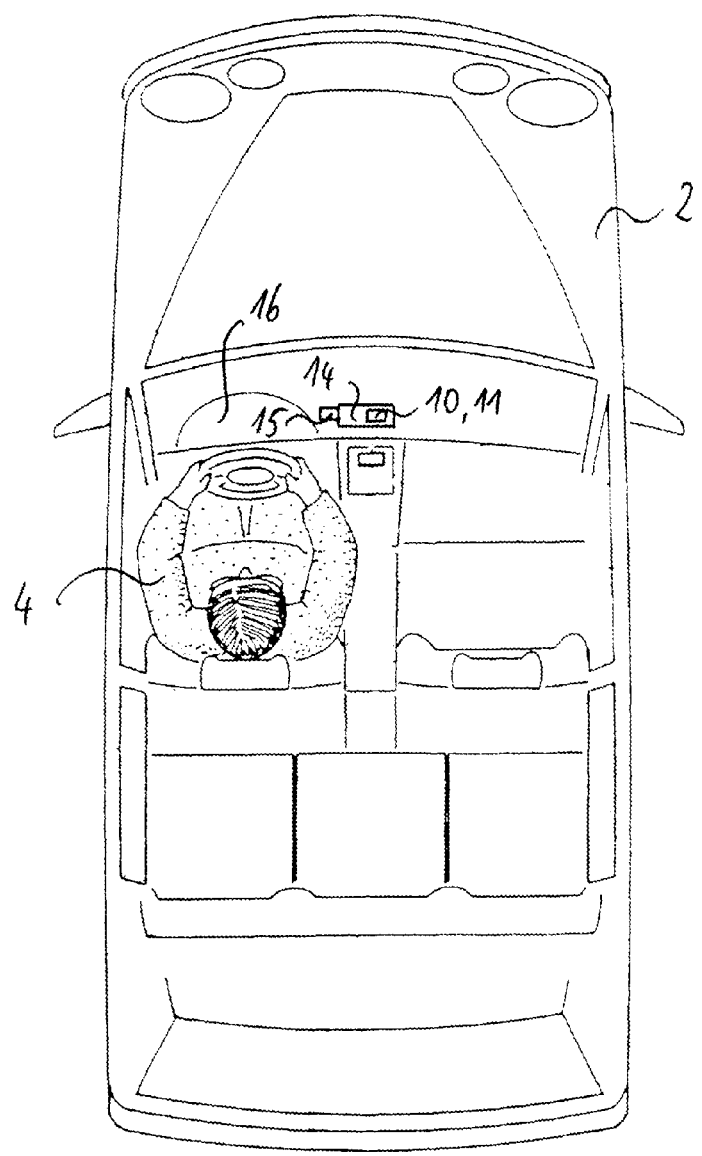
FIGS. 3A and 3B show a motor vehicle according to an embodiment.
Figure 3B:
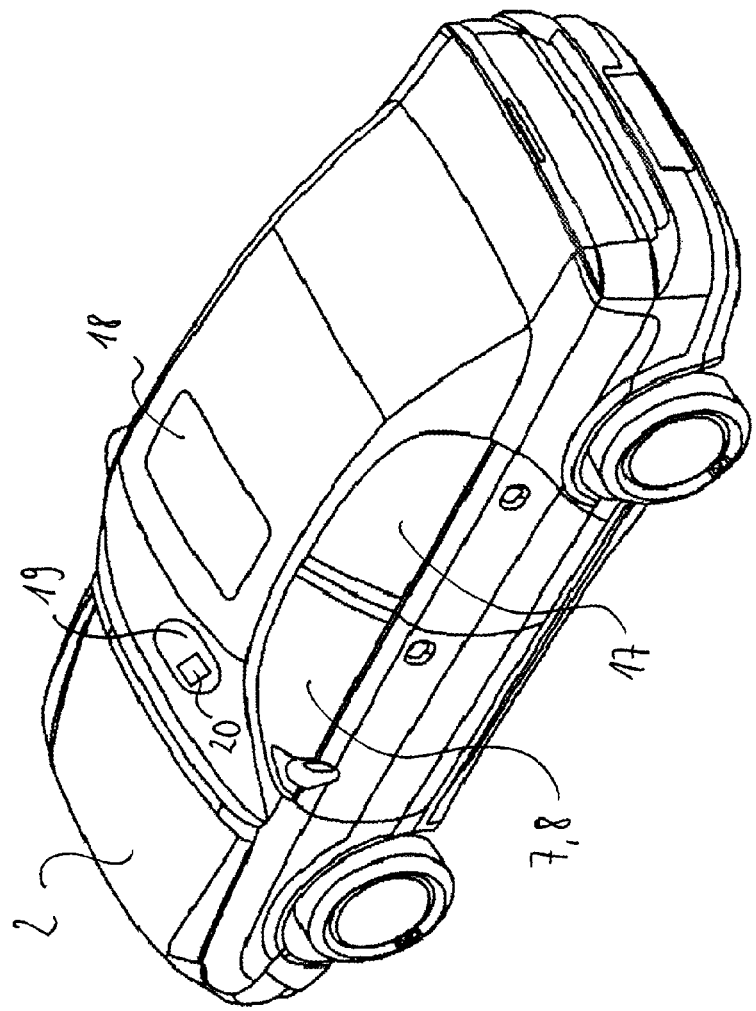

FIG. 3A and FIG. 3B show a motor vehicle 2 according to an embodiment of the application. FIG. 3A shows a schematic top view, the roof of the motor vehicle 2 not being shown in order to be able to illustrate the interior of the motor vehicle 2 in the top view shown. FIG. 3B shows a schematic perspective view of the motor vehicle 2. In the embodiment shown, the motor vehicle 2 is a passenger automobile and has a driver assistance system explained in greater detail in connection with the following figure.

In FIG. 3A, a sensor 10, which is implemented in the embodiment shown as a rain sensor 11 and is arranged in the area of an interior rearview mirror 14 of the motor vehicle 2, as well as an optical camera 15, which is arranged adjacent to the interior rearview mirror 14, and an instrument cluster 16 of the motor vehicle 2 are shown. The optical camera 15 is oriented having its acquisition area in the direction of a driver 4 of the motor vehicle 2 in such a manner that the acquisition area includes the area of the face of the driver 4. A closing frequency of the eyelids of the driver 4 and/or a closing speed of the eyelids of the driver 4 can thus be ascertained by means of the images recorded by the optical camera 15. A degree of fatigue of the driver 4 can be ascertained based on the mentioned parameters.

If the ascertained degree of fatigue of the driver 4 exceeds a first predetermined threshold value, at least partial opening of a window 7 shown in FIG. 3B, which forms a side window 8 arranged on the driver's side in a front area of the motor vehicle 2, is performed by the driver assistance system of the motor vehicle 2 explained in greater detail in connection with FIG. 4. Furthermore, at least partial opening of the further windows of the motor vehicle 2, for example, a window 17 arranged on the driver's side in a rear area of the motor vehicle 2, which is shown in FIG. 3B, or at least partial opening of a roof opening system 18, can be performed, if the ascertained degree of fatigue of the driver 4 exceeds the first predetermined threshold value. Furthermore, a display device 20 of an information and entertainment system 19 of the motor vehicle 2 is shown in FIG. 3B.

Figure 4:
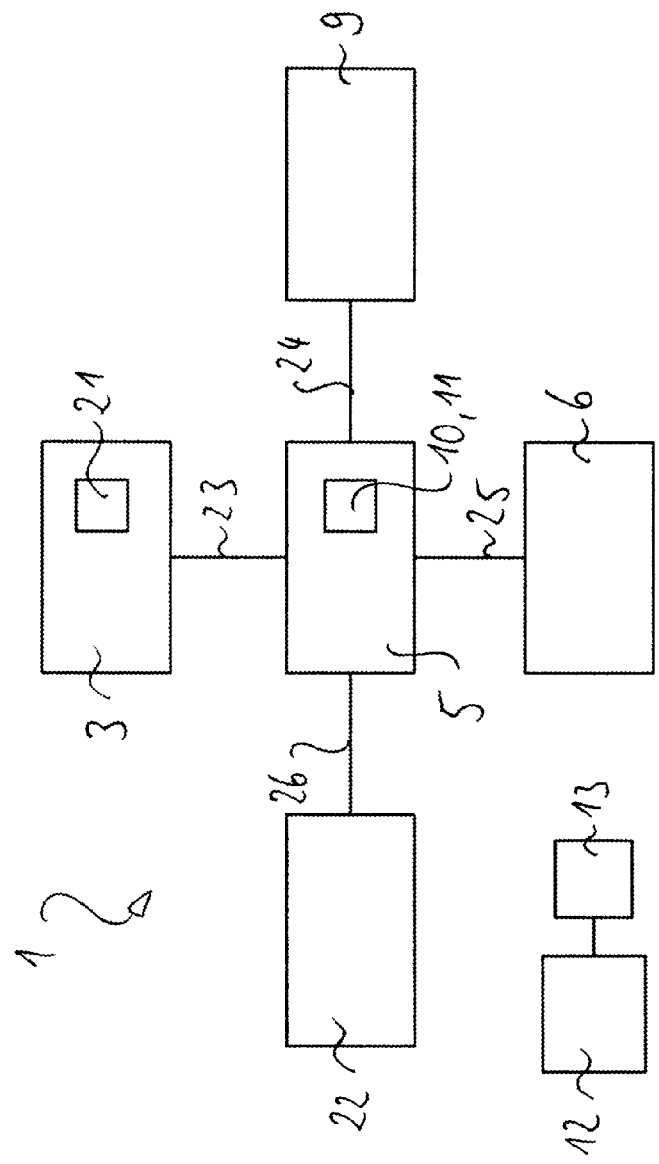
FIG. 4 shows a driver assistance system according to an embodiment.

FIG. 4 shows a driver assistance system 1 of the motor vehicle shown in FIG. 3A and FIG. 3B according to an embodiment. Components having the same functions as in FIG. 3A and FIG. 3B are identified by the same reference numerals and are not explained again hereafter. The driver assistance system 1 has a first ascertainment device 3, which is implemented to ascertain at least one parameter that characterizes a possible fatigue of the current driver of the motor vehicle. For this purpose, the first ascertainment device 3 has a sensor 21, in the embodiment shown in the form of the optical camera shown in FIG. 3A.

In addition, the driver assistance system 1 has a second ascertainment device 5, which is implemented to ascertain a degree of fatigue of the driver based on the at least one ascertained parameter. The second ascertainment device 5 is connected for this purpose via a signal line 23 to the first ascertainment device 3. In addition, the second ascertainment device 5 is implemented in the embodiment shown to ascertain a current weather situation in the surroundings of the motor vehicle by means of data of at least one sensor 10, which is implemented in the embodiment shown as an opto-electronic and/or capacitive rain sensor 11.

Furthermore, the driver assistance system 1 has an opening device 6, which is implemented to at least partially open at least one window of the motor vehicle, if the ascertained degree of fatigue of the driver exceeds a first predetermined threshold value and if it is ascertained that the current weather situation in the surroundings of the motor vehicle is free of precipitation. The opening device 6 has an electric positioning motor (not shown in greater detail) and is connected via a control and signal line 25 to the second ascertainment device 5 for this purpose in the embodiment shown.

The driver assistance system 1 is additionally implemented to reduce a temperature, which is set by means of an air conditioner 9 of the motor vehicle, of at least one subarea of the interior of the motor vehicle and to increase a fresh air component, which is set by means of the air conditioner 9 of the motor vehicle, of at least one subarea of the interior of the motor vehicle, if the ascertained degree of fatigue of the driver exceeds the first predetermined threshold value. Furthermore, the driver assistance system 1 is implemented to increase a direct flow against the driver using fresh air, which is provided by means of the air conditioner 9, if the ascertained degree of fatigue of the driver exceeds the first predetermined threshold value. The second ascertainment device 5 is connected via a control and signal line 24 to the air conditioner 9 for this purpose.

In addition, the driver assistance system 1 is implemented to output a first warning message if the ascertained degree of fatigue of the driver exceeds the first predetermined threshold value. For this purpose, the second ascertainment device 5 is connected via a control and signal line 26 to an output device 22, which is implemented as an optical and/or acoustic and/or haptic output device. The output device 22 can be a component of the instrument cluster of the motor vehicle shown in FIG. 3A, for example. Furthermore, the output device 22 can be a component of the information and entertainment system of the motor vehicle shown in FIG. 3B.

Furthermore, the driver assistance system 1 is implemented in the embodiment shown to output a second warning message, if the ascertained degree of fatigue of the driver exceeds a second predetermined threshold value, the second predetermined threshold value being less than the first predetermined threshold value. The second warning message can again be output as an optical and/or acoustic and/or haptic warning message. In addition, in the embodiment shown, the driver assistance system 1 has a computer unit 12 and a computer-readable medium 13, a computer program product being stored on the computer-readable medium 13, which, when it is executed on the computer unit 12, instructs the computer unit 12 to execute the steps mentioned in connection with the embodiments of the method. For this purpose, the computer unit 12 is directly or indirectly connected to the corresponding elements in a way not shown in greater detail.

While at least one exemplary embodiment has been presented in the foregoing summary and detailed description, it should be appreciated that a vast number of variations exist. It should also be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalents.

What is claimed is:

1. A driver assistance system for a motor vehicle comprising:
   sensors determining an ambient air temperature outside the motor vehicle, an interior temperature of the motor vehicle, and a current weather condition surrounding the motor vehicle;
   a first ascertainment device configured to ascertain at least one parameter that characterizes a driver fatigue;
   a second ascertainment device configured to ascertain a degree of driver fatigue based on the at least one parameter; and
   an opening device configured to at least partially open at least one window of the motor vehicle when the degree of driver fatigue exceeds a first predetermined threshold value, when the current weather condition surrounding the motor vehicle is substantially free of precipitation, and when the interior temperature of the motor vehicle is greater than the ambient air temperature outside the motor vehicle.

2. The driver assistance system according to claim 1, wherein the at least one window is a side window arranged on a driver side in a front area of the motor vehicle.

3. The driver assistance system according to claim 1, wherein the driver assistance system is further configured to reduce a temperature that is set with an air conditioner of the motor vehicle if the degree of driver fatigue exceeds the first predetermined threshold value.

4. The driver assistance system according to claim 3, wherein a subarea of an interior of the motor vehicle at least partially includes an area of driver surroundings.

5. The driver assistance system according to claim 3, wherein the driver assistance system is further configured to increase a direct flow of fresh air that is provided with the air conditioner of the motor vehicle when the degree of driver fatigue exceeds the first predetermined threshold value.

6. The driver assistance system according to claim 1, wherein the at least one sensor is a rain sensor.

7. The driver assistance system according to claim 1, wherein the at least one parameter that characterizes the driver fatigue is a closing frequency of at least one eyelid of the driver.

8. A method for operating a driver assistance system of a motor vehicle, comprising:
 ascertaining a temperature of an ambient air outside the motor vehicle and a temperature of an interior of the motor vehicle;
 ascertaining a current weather condition surrounding the motor vehicle;
 ascertaining at least one parameter that characterizes a driver fatigue;
 ascertaining a degree of the driver fatigue based on the at least one parameter; and
 at least partially opening at least one window of the motor vehicle with at least one opening device when the degree of the driver fatigue exceeds a first predetermined threshold value, when the current weather condition surrounding the motor vehicle is substantially free of precipitation, and when the temperature of the interior of the motor vehicle is greater than the temperature of the ambient air outside the motor vehicle.

9. The method according to claim 8, further comprising generating a first warning message when the degree of the driver fatigue exceeds the first predetermined threshold value.

10. The method according to claim 9, further comprising:
 generating a second warning message when the degree of the driver fatigue exceeds a second predetermined threshold value,
 wherein the second predetermined threshold value is less than the first predetermined threshold value.

11. A non-transitory computer readable medium embodying a computer program product, said computer program product comprising:
 an operating program for operating a driver assistance system of a motor vehicle, the operating program configured to:
 ascertain a temperature of an ambient air outside the motor vehicle and a temperature of an interior of the motor vehicle;
 ascertain a current weather condition surrounding the motor vehicle;
 ascertain at least one parameter that characterizes a driver fatigue;
 ascertain a degree of the driver fatigue based on the at least one parameter; and
 at least partially open at least one window of the motor vehicle with at least one opening device when the degree of the driver fatigue exceeds a first predetermined threshold value, when the current weather condition surrounding the motor vehicle is substantially free of precipitation, and when the temperature of the interior of the motor vehicle is greater than the temperature of the ambient air outside the motor vehicle.

12. The non-transitory computer readable medium embodying the computer program product claim 11, the operating program further configured to generate a first warning message when the degree of the driver fatigue exceeds the first predetermined threshold value.

13. The non-transitory computer readable medium embodying the computer program product claim 11, the operating program further configured to:
 generate a second warning message when the degree of the driver fatigue exceeds a second predetermined threshold value,
 wherein the second predetermined threshold value is less than the first predetermined threshold value.

* * * * *